(12) United States Patent
Klimko

(10) Patent No.: US 7,745,461 B1
(45) Date of Patent: Jun. 29, 2010

(54) METHOD OF TREATING DRY EYE DISORDERS

(75) Inventor: Peter G. Klimko, Fort Worth, TX (US)

(73) Assignee: Alcon Research, Ltd., Fort Worth, TX (US)

(*) Notice: Subject to any disclaimer, the term of this patent is extended or adjusted under 35 U.S.C. 154(b) by 602 days.

(21) Appl. No.: 11/678,655

(22) Filed: Feb. 26, 2007

Related U.S. Application Data

(60) Provisional application No. 60/777,063, filed on Feb. 27, 2006.

(51) Int. Cl.
  *A61K 31/47* (2006.01)
(52) U.S. Cl. .................. 514/309; 514/307; 514/912
(58) Field of Classification Search ............. 514/307, 514/309, 912
  See application file for complete search history.

(56) References Cited

U.S. PATENT DOCUMENTS

| | | | |
|---|---|---|---|
| 4,131,651 A | 12/1978 | Shah et al. | 424/78 |
| 4,370,325 A | 1/1983 | Packman | 424/245 |
| 4,409,205 A | 10/1983 | Shively | 424/78 |
| 4,744,980 A | 5/1988 | Holly | 424/78 |
| 4,818,537 A | 4/1989 | Guo | 424/427 |
| 4,883,658 A | 11/1989 | Holly | 424/80 |
| 4,914,088 A | 4/1990 | Glonek et al. | 514/76 |
| 4,966,773 A | 10/1990 | Gressel et al. | 424/489 |
| 5,041,434 A | 8/1991 | Lubkin | 514/182 |
| 5,075,104 A | 12/1991 | Gressel et al. | 424/78.04 |
| 5,174,988 A | 12/1992 | Mautone et al. | 424/45 |
| 5,278,151 A | 1/1994 | Korb et al. | 514/76 |
| 5,290,572 A | 3/1994 | MacKeen | 424/602 |
| 5,294,607 A | 3/1994 | Glonek et al. | 514/76 |
| 5,371,108 A | 12/1994 | Korb et al. | 514/762 |
| 5,578,586 A | 11/1996 | Glonek et al. | 514/76 |
| 5,620,995 A | 4/1997 | Weidmann et al. | 514/350 |
| 5,696,166 A | 12/1997 | Yanni et al. | 514/573 |
| 5,719,164 A | 2/1998 | Weidmann et al. | 514/312 |
| 5,800,807 A | 9/1998 | Hu et al. | 424/78.04 |
| 5,916,898 A | 6/1999 | Edwards et al. | 514/292 |
| 5,958,912 A | 9/1999 | Sullivan | 514/177 |
| 6,020,350 A | 2/2000 | Weidmann et al. | 514/346 |
| 6,093,730 A | 7/2000 | Weidmann et al. | 514/309 |
| 6,153,607 A | 11/2000 | Pflugfelder et al. | 514/178 |
| 2004/0058875 A1 | 3/2004 | Gamache | 514/15 |
| 2004/0235082 A1 | 11/2004 | Fourney et al. | 435/23 |
| 2004/0254215 A1 | 12/2004 | Arend et al. | 514/310 |

FOREIGN PATENT DOCUMENTS

| | | |
|---|---|---|
| WO | WO 00/03705 | 1/2000 |
| WO | WO2007/009044 | 1/2007 |

OTHER PUBLICATIONS

Ang et al, "Dry eye after refractive surgery," *Current Opinion Ophthalmology*, vol. 12, pp. 318-322 (2001).

Coassin et al., "Efficacy of topical nerve growth factor treatment in dogs affected by dry eye," *Graefe's Archives Clinical Experimental Ophthalmology*, vol. 243, pp. 151-155 (2005).

Esquenazi et al., "Topical Combination of NGF and DHA Increases Rabbit Corneal Nerve Regeneration after Photorefractive Keratectomy," *Investivative Opthalmology Visual Science*, vol. 46(9), pp. 3121-3127 (2005).

Ivan et al., "Biochemical purification and pharmacological inhibition of a mammalian prolyl hydroxylase acting on hypoxia-inducible factor," *PNAS*, vol. 99(21), pp. 13459-13464 (2002).

Joo et al., The Effect of Nerve Growth Factor on Corneal Sensitivity After Laser in Situ Keratomileusis, *Arch Ophthalmology*, vol. 122, pp. 1338-1341 (2004).

Lee et al., "Neuronal apoptosis linked to EgIN3 prolyl hydroxylase and familial pheochromocytoma genes: Developmental culling and cancer," *Cancer Cell*, vol. 8, pp. 155-167 (2005).

Lemp et al., "Report of the National Eye Institute/Industry Workshop on Clinical Trials in Dry Eyes," *CLAO Journal*, vol. 21(4), pp. 221-231 (1995).

Li et al., "JNK and ERK MAP kinases mediate induction of IL-1β, TNF-α and IL-8 following hyperosmolar stress in human limbal epithelial cells," *Experimental Eye Research*, vol. 82, pp. 588-596 (2006).

Lipscomb et al., "Expression of the SM-20 Gene Promotes Death in Nerve Growth Factor-Dependent Sympathetic Neurons," *J. Neurochemistry*, vol. 73(1), pp. 429-432 (1999).

Lipscomb et al., "SM-20 Is a Novel Mitochondrial Protein That Causes Caspase-dependent Cell Death in Nerve Growth Factor-dependent Neurons," *The Journal of Biological Chemistry*, vol. 276 (7), pp. 5085-5092 (2001).

Marsh et al., Topical Nonpreserved Methylprednisolone Therapy for Keratoconjunctivitis Sicca in Sjögren Syndrome, *Ophthalmology*, vol. 106, pp. 811-816 (1999).

McCulley et al., "Tear Film Structure and Dry Eye," *Contactologia*, vol. 20, pp. 145-149 (1998).

Pepose et al., "Is There a Role for Neurotrophin Treatment of the Ocular Surface Following Laser in Situ Keratomileusis (LASIK)?," *American Joournal of Ophthalmology*, vol. 139 (6), pp. 1090-1094 (2005).

Peso et al., "The von Hippel Lindau/Hypoxia-inducible Factor (HIF) Pathway Regulates the Transcription of the HIF-Proline Hydroxylase Genes in Response to Low Oxygen," *The Journal of Biological Chemistry*, vol. 278(49), pp. 4869048695 (2003).

Schlingensiepen et al., "The Role of Jun Transcription Factor Expression and Phosphorylation in Neuronal Differentiation, Neuronal Cell Death, and Plastic Adaptations in Vivo," *Cell Molecular Neurobiology*, vol. 14(5), pp. 487-505 (1994).

Shine et al., Keratoconjunctivitis Sicca Associated with Meibomian Secretion Polar Lipid Abnormality, *Archives of Ophthalmology*, vol. 116, pp. 849-852 (1998).

Song et al., "Neurturin-Deficient Mice Develop Dry Eye and Keratoconjunctivitis Sicca," *Investivative Ophthalmology & Visual Science*, vol. 44(10), pp. 4223-4229 (2003).

Straub et al., "Induction of SM-20 in PC12 cells leads to increased cytochrome c levels, accumulation of cytochrome c in the cytosol, and caspase-dependent cell death," *J. Neurochemistry*, vol. 85(2), pp. 318-328 (2003).

(Continued)

*Primary Examiner*—Zohreh A Fay
(74) *Attorney, Agent, or Firm*—Patrick M. Ryan

(57) ABSTRACT

The topical use of EgLN-3 inhibitors is disclosed for the treatment of dry eye.

4 Claims, No Drawings

OTHER PUBLICATIONS

Tauber et al., *Lacrimal Gland, Tear Film and Dry Eye Syndromes 2*, Plenum Press, New York (1998), "A Dose-Ranging Clinical Trial to Assess the Safety and Efficacy of Cyclosporine Ophthalmic Emulsion in Patients with Keratoconjunctivitis Sicca," pp. 969-972.

Zhang et al., Altered Corneal Nerves in Aqueous Tear Deficiency Viewed by in Vivo Confocal Microscopy, *Cornea*, vol. 24(7), pp. 818-824 (2005).

Zoukhri et al., "c-Jun $HN_2$-terminal kinase mediates interleukin-1β-induced inhibition of lacrinal gland secretion," *Journal of Neurochemistry*, vol. 96(1), pp. 126-135 (2006).

METHOD OF TREATING DRY EYE DISORDERS

This application claims priority to U.S. Provisional Application, U.S. Ser. No. 60/777,063 filed Feb. 27, 2006.

The present invention is directed to the treatment of dry eye disorders. In particular, the present invention is directed toward the use of inhibitors of the enzyme EgLN-3 to treat dry eye in mammals.

BACKGROUND OF THE INVENTION

Dry eye, also known generically as keratoconjunctivitis sicca, is an ocular surface disease characterized by tear film compositional/rheological abnormalities and excessive inflammation that leads to dysregulation of the corneal and conjunctival epithelial cell barrier function. It is a common opthalmological disorder affecting millions of Americans each year. The condition is particularly widespread among post-menopausal women due to hormonal changes following the cessation of fertility. Dry eye may afflict an individual with varying severity. In mild cases, a patient may experience burning, a feeling of dryness, and persistent irritation such as is often caused by small bodies lodging between the eye lid and the eye surface. In severe cases, vision may be substantially impaired. Other diseases, such as Sjogren's disease and cicatricial pemphigoid manifest dry eye complications.

Although it appears that dry eye may result from a number of unrelated pathogenic causes, all presentations of the complication share a common effect, that is the breakdown of the pre-ocular tear film, which results in dehydration of the exposed outer surface and many of the symptoms outlined above (Lemp, *Report of the National Eye Institute/Industry Workshop on Clinical Trials in Dry Eyes, The CLAO Journal*, volume 21, number 4, pages 221-231 (1995)).

Practitioners have taken several approaches to the treatment of dry eye. One common approach has been to supplement and stabilize the ocular tear film using so-called artificial tears instilled throughout the day. Other approaches include the use of ocular inserts that provide a tear substitute or stimulation of endogenous tear production.

Examples of the tear substitution approach include the use of buffered, isotonic saline solutions, aqueous solutions containing water soluble polymers that render the solutions more viscous and thus less easily shed by the eye. Tear reconstitution is also attempted by providing one or more components of the tear film such as phospholipids and oils. Phospholipid compositions have been shown to be useful in treating dry eye; see, e.g., McCulley and Shine, *Tear film structure and dry eye, Contactologia*, volume 20(4), pages 145-49 (1998); and Shine and McCulley, *Keratoconjunctivitis sicca associated with meibomian secretion polar lipid abnormality, Archives of Ophthalmology*, volume 116(7), pages 849-52 (1998). Examples of phospholipid compositions for the treatment of dry eye are disclosed in U.S. Pat. No. 4,131,651 (Shah et al.), U.S. Pat. No. 4,370,325 (Packman), U.S. Pat. No. 4,409,205 (Shively), U.S. Pat. No. 4,744,980 and U.S. Pat. No. 4,883,658 (Holly), U.S. Pat. No. 4,914,088 (Glonek), U.S. Pat. No. 5,075,104 (Gressel et al.), U.S. Pat. No. 5,278,151 (Korb et al.), U.S. Pat. No. 5,294,607 (Glonek et al.), U.S. Pat. No. 5,371,108 (Korb et al.) and U.S. Pat. No. 5,578,586 (Glonek et al.). U.S. Pat. No. 5,174,988 (Mautone et al.) discloses phospholipid drug delivery systems involving phospholipids, propellants and an active substance.

Another approach involves the provision of lubricating substances in lieu of artificial tears. For example, U.S. Pat. No. 4,818,537 (Guo) discloses the use of a lubricating, liposome-based composition, and U.S. Pat. No. 5,800,807 (Hu et al.) discloses compositions containing glycerin and propylene glycol for treating dry eye.

Although these approaches have met with some success, problems in the treatment of dry eye nevertheless remain. The use of tear substitutes, while temporarily effective, generally requires repeated application over the course of a patient's waking hours. It is not uncommon for a patient to have to apply artificial tear solution ten to twenty times over the course of the day. Such an undertaking is not only cumbersome and time consuming, but is also potentially very expensive. Transient symptoms of dry eye associated with refractive surgery have been reported to last in some cases from six weeks to six months or more following surgery.

Aside from efforts directed primarily to the alleviation of symptoms associated with dry eye, methods and compositions directed to treatment of the dry eye condition have also been pursued. For example, U.S. Pat. No. 5,041,434 (Lubkin) discloses the use of sex steroids, such as conjugated estrogens, to treat dry eye conditions in post-menopausal women; U.S. Pat. No. 5,290,572 (MacKeen) discloses the use of finely divided calcium ion compositions to stimulate pre-ocular tear film production; and U.S. Pat. No. 4,966,773 (Gressel et al.) discloses the use of microfine particles of one or more retinoids for ocular tissue normalization.

Some recent literature reports suggest that patients suffering from dry eye syndrome disproportionately exhibit the hallmarks of excessive inflammation in relevant ocular tissues, such as the lacrimal and meibomian glands. The use of various compounds to treat dry eye patients, such as steroids [e.g. U.S. Pat. No. 5,958,912; Marsh, et al., *Topical nonpreserved methylprednisolone therapy for keratoconjunctivitis sicca in Sjogren syndrome, Ophthalmology*, 106(4): 811-816 (1999); Pflugfelder, et. al. U.S. Pat. No. 6,153,607], cytokine release inhibitors (Yanni, J. M.; et. al. WO 0003705 A1), cyclosporine A [Tauber, *J. Adv. Exp. Med. Biol.* 1998, 438 (Lacrimal Gland, Tear Film, and Dry Eye Syndromes 2), 969], and 15-HETE (Yanni et. al., U.S. Pat. No. 5,696,166), has been disclosed.

The EgLN enzyme family are 2-oxoglutarate-dependent prolyl hydroxylases that catalyze the constitutive hydroxylation of the HIF-1α protein under normoxic conditions [Peso et al., *J. Biol. Chem.* 2003, 278(49), 48690-48695; Ivan et al., *PNAS* 2002, 99(21), 13459-13464]. The hydroxylated HIF-1α protein is targeted for polyubiquination and proteasomal degradation by pVHL, the protein product of the von Hippel-Landau gene. Under hypoxic conditions, oxygen concentration becomes rate-limiting and EgLN-catalyzed hydroxylation is inefficient. Consequently HIF-1α escapes destruction and forms a heterodimer with HIF-1β. The complex is transported to the nucleus, where it acts as a transcription factor to up-regulate production of hypoxia-induced proteins and growth factors, especially VEGF.

The EgLN-3 isozyme also appears to be involved as an effector of apoptosis in sympathetic neurons under certain conditions. In particular, EgLN-3 is a downstream effector of nerve growth factor (NGF) withdrawal-induced apoptosis in NGF-dependent neurons. Expression of SM-20, a rat ortholog of EgLN-3, increases after NGF withdrawal in sympathetic neurons [Lipscomb et al., *J Neurochem.* 1999, 73(1), 429-432]. Induced expression of SM-20 causes apoptosis in sympathetic neurons even in the presence of NGF in a caspase-dependent process [*J Neurochem.* 2003, 85(2), 318-328]. Although SM-20 is normally resident in the mitochondria, a truncated form that localizes to the cytoplasm due to loss of a mitochondrial targeting sequence still induces apoptosis [Lipscomb et al., *J Biol Chem.* 2001, 276(7), 5085-5092].

These findings have recently been extended to developing neurons [Lee et al., *Cancer Cell* 2005, 8, 155-167]. During embryogenesis, sympathetic neuronal precursor cells that fail to make synaptic connections are starved of NGF and undergo c-Jun-dependent apoptosis [Schlingensiepen et al., *Cell Mol. Neurobiol.* 1994, 14, 487-505]. The risk of a type of neuronal cancer called familial pheochromocytoma is increased by germline mutations that inactivate pVHL or NF1 (an antagonist of the NGF receptor TrkA), or that activate c-RET (the receptor for glial derived neurotrophic factor, which cross-talks with TrkA). In each of these cases the intracellular concentration of the c-Jun antagonist JunB increases, inhibiting apoptosis. Germline mutations that reduce the activity of succinate dehydrogenase (SDH) also increase familial pheochromocytoma risk. Succinate is a coproduct of EgLN-3-catalyzed proline hydroxylation and feedback inhibits the enzyme, and thus needs to be removed by SDH for EgLN-3 prolyl hydroxylase activity. Sporadic pheochromocytoma due to somatic mutation in one of these genes is rare since apoptosis of "unconnected" sympathetic neuronal precursor cells is not important once embryogenesis is complete.

NGF withdrawal-induced apoptosis requires EgLN-3 proline hydroxylase activity. EgLN-3-induced cell death is not reduced by co-expression of JunB. Additionally, EgLN-3 expression knockdown by siRNA inhibits c-Jun induced cell death. These observations indicate that EgLN-3 is necessary and sufficient for NGF withdrawal-induced apoptosis, and acts downstream of c-Jun. The presumed protein target of EgLN-3-catalyzed proline hydroxylation that is important for apoptosis induction has not been identified, although it is suspected that pVHL's polyubiquination (and subsequent marking for proteasomal destruction) of a hyperphosphorylated form of atypical protein kinase C is responsible for pVHL's suppression of JunB.

Corneal nerves likely play a key role in maintaining homeostasis of the ocular surface by communicating with brain regarding required lacrimal gland support. In support of this theory, it has been observed that patients that undergo LASIK refractive surgery (where corneal nerves are severed) suffer from an increased incidence of dry eye [see for example: Ang, R. T.; Dartt, D. A.; Tsubota, K. *Curr. Opin. Opthalmol.* 2001, 12(4), 318-322]. Patients who suffer from dry eye have been reported to have aberrant corneal nerve morphology [Zhang et al., *Cornea.* 2005, 24(7), 818-824]. Mice deficient in the neurotrophic factor neurturin develop the characteristics of dry eye [Song et al., *Invest. Opthalmol. Vis. Sci.* 2003, 44(10), 4223-4229].

If corneal nerve dysfunction plays a role in dry eye disease pathology, then neurotrophic factors may represent a potential treatment [for a discussion, see: Pepose and Johnson, *Am. J. Opthalmol.* 2005, 139(6), 1090-1094]. Topical application of NGF has been reported to accelerate corneal innervation [Bazan and co-workers, *Investigative Ophthalmology and Visual Science* 2005, 46(9), 3121-3127; in this case the effect was synergistic in combination with the polyunsaturated fatty acid DHA] and enhance corneal sensitivity [Joo et al., *Arch. Opthalmol.* 2004, 122(9), 1338-1341] in rabbit models of refractive surgery, while treatment of dogs suffering from dry eye with topical NGF has been disclosed to improve tear quality, resolve corneal haze, and increase conjunctival goblet cell density [Coassin et al., *Graefes Arch. Clin. Exp. Opthalmol.* 2005, 243(2), 151-155].

The c-jun N-terminal kinase (JNK) pathway may play an important role in dry eye disease pathology. For example, JNK inhibition has been reported to reduce expression of IL-1β, TNF-α, and IL-8 induced by hyperosmolar stress in human limbal epithelial cells [Pflugfelder and co-workers, *Exp. Eye Res.* 2005, in press] and to increase tear production in a mouse model of dry eye [Zoukhri et al., *J. Neurochem.* 2006, 96(1), 126-135], and JNK inhibitors have been claimed for the treatment of dry eye (Gamache, US Published Patent Application, US 2004058875 A1).

The use of certain EgLN-3 enzyme inhibitors for the treatment of obesity (Fourney et al., U.S. Published Patent Application US2004/0235082A1), anemia via increasing endogenous erythropoietin production (Arend et al., U.S. Published Patent Application US2004/0254215A1), and fibrotic diseases (Weidmann et al., U.S. Pat. Nos. 6,093,730 and 5,719,164)), has been disclosed. Additionally, the use of certain EgLN-3 enzyme inhibitors has been disclosed for the postoperative treatment of glaucoma operations (ostensibly to maintain the filtration bleb) (Wiedmann et al., U.S. Pat. No. 6,020,350). However the use of the compounds of the present invention for the treatment of dry eye has not been disclosed.

SUMMARY OF THE INVENTION

The present invention is directed to methods for the treatment of dry eye. According to the methods of the present invention, an EgLN-3 inhibitor is administered to a patient. A compound of the present invention is preferably administered in an ophthalmic composition dosed topically to a patient's eye.

DETAILED DESCRIPTION OF THE INVENTION

Unless indicated otherwise, all component amounts are presented on a % (w/v) basis.

According to the methods of the present invention, a composition comprising a compound of formulae A-H is topically administered to a mammal in need thereof:

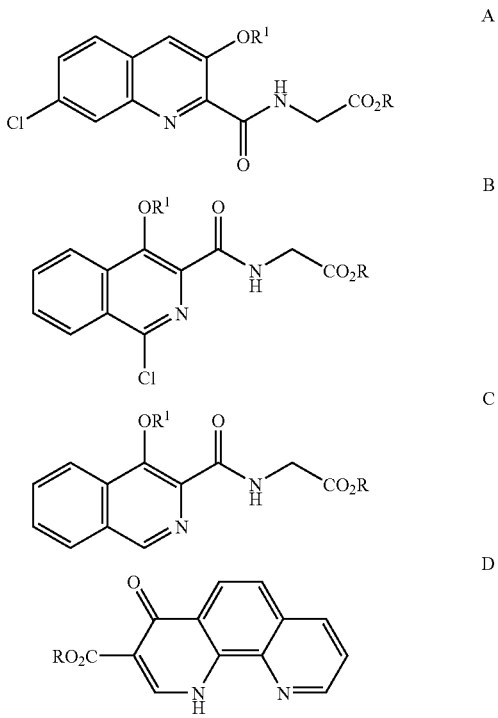

-continued

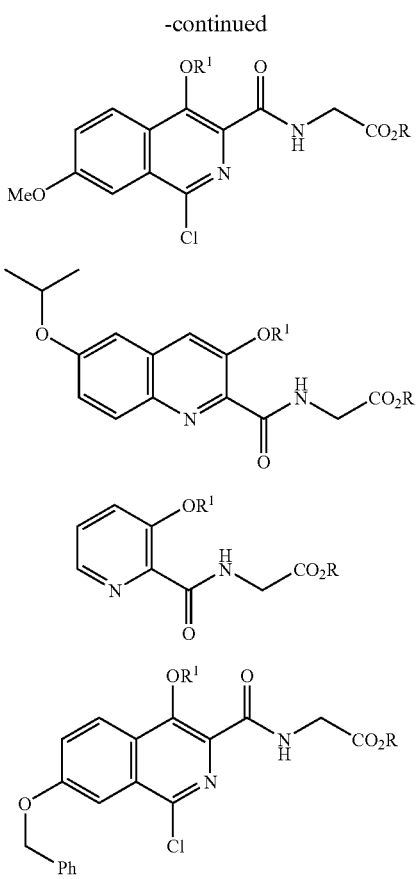

wherein

R is H, $C_{1-6}$ straight chain or branched alkyl, phenyl, or benzyl, or $CO_2R$ forms a salt of formula $CO_2^-M^+$, with $M^+$ being $Li^+$, $Na^+$, $K^+$, or $NH_4^+$; and $R^1$ is H, $C(O)CH_3$, or $C(O)C_6H_5$.

Preferred are compounds of formulae A-H with R being H, $CH_3$, $C_2H_5$, or $i-C_3H_7$, and $R^1$ being H or $C(O)CH_3$. Especially preferred are compounds B and G with R being H, $CH_3$, $C_2H_5$, or $i-C_3H_7$, and $R^1$ being H or $C(O)CH_3$.

The compounds of formulae A-H with both R and $R^1$=H can be synthesized according to the following literature examples tabulated below.

| Compound Formula | Synthesis Reference |
| --- | --- |
| A | Weidmann et al., U.S. Pat. No. 5,719,164 |
| B | Weidmann et al., U.S. Pat. No. 6,093,730 |
| C | Arend et al., U.S. Published patent application Ser. No. 2004/0,254,215 A1 |
| D | Edwards et al., U.S. Pat. No. 5,916,898 |
| E | Weidmann et al., U.S. Pat. No. 6,093,730 |
| F | Weidmann et al., U.S. Pat. No. 5,719,164 |
| G | Weidmann et al., U.S. Pat. No. 5,620,995 |
| H | Weidmann et al., U.S. Pat. No. 6,093,730 |

According to the methods of the present invention, an EgLN-3 inhibitor is administered in a pharmaceutically acceptable carrier, preferably via topical ophthalmic administration. The compositions are formulated in accordance with methods known in the art. The compositions may contain more than one an EgLN-3 inhibitor. Additionally, the compositions may contain a second drug, other than an EgLN-3 inhibitor.

The compositions of the present invention contain a pharmaceutically effective amount of an EgLN-3 inhibitor. As used herein, "a pharmaceutically effective amount" means an amount sufficient to reduce or eliminate dry eye symptoms. Generally, the compositions of the present invention will contain from 0.01% to 3% of an EgLN-3 inhibitor. Preferably, the compositions of the present invention will contain from 0.1% to 2% of an EgLN-3 inhibitor.

The compositions administered according to the present invention may also include various other ingredients, including but not limited to surfactants, tonicity agents, buffers, preservatives, co-solvents and viscosity building agents.

Various tonicity agents may be employed to adjust the tonicity of the composition, preferably to that of natural tears for ophthalmic compositions. For example, sodium chloride, potassium chloride, magnesium chloride, calcium chloride, dextrose and/or mannitol may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm/Kg, preferably 250-350 mOsm/Kg).

An appropriate buffer system (e.g., sodium phosphate, sodium acetate, sodium citrate, sodium borate or boric acid) may be added to the compositions to prevent pH drift under storage conditions. The particular concentration will vary, depending on the agent employed. Preferably, however, the buffer will be chosen to maintain a target pH within the range of pH 5.5-8.

Other compounds designed to lubricate, "wet," approximate the consistency of endogenous tears, aid in natural tear build-up, or otherwise provide temporary relief of dry eye symptoms and conditions upon ocular administration to the eye are known in the art and may be included in the compositions of the present invention. Such compounds may enhance the viscosity of the composition, and include, but are not limited to: monomeric polyols, such as, glycerol, propylene glycol, ethylene glycol; polymeric polyols, such as, polyethylene glycol, hydroxypropylmethyl cellulose ("HPMC"), carboxy methylcellulose sodium, hydroxy propylcellulose ("HPC"), dextrans, such as, dextran 70; water soluble proteins, such as gelatin; and vinyl polymers, such as, polyvinyl alcohol, polyvinylpyrrolidone, povidone and carbomers, such as, carbomer 934P, carbomer 941, carbomer 940, carbomer 974P.

Topical ophthalmic products are typically packaged in multidose form. Preservatives are typically required to prevent microbial contamination during use. Suitable preservatives include: benzalkonium chloride, chlorobutanol, benzododecinium bromide, methyl paraben, propyl paraben, phenylethyl alcohol, edetate disodium, sorbic acid, polyquarternium-1, or other agents known to those skilled in the art. Such preservatives are typically employed at a level of from 0.001 to 1.0% w/v. Unit dose compositions of the present invention will be sterile, but typically will not contain a preservative and will be unpreserved.

Generally, 1-2 drops of such compositions will be administered from once to many times per day.

A representative eye drop formulation is provided below in Example 1 for treating dry eye.

| Ingredient | Concentration (% w/v) |
|---|---|
| Compound of formula A-H | 0.1-1.0 |
| Hydroxypropyl methylcellulose | 0.1-0.5 |
| Dextran 70 | 0.1 |
| Sodium Chloride | 0.8 |
| Potassium Chloride | 0.12 |
| Dibasic Sodium Phosphate | 0.025 |
| Edetate Disodium | 0.01 |
| Polyquaternium-1 | 0.001-0.005 |
| NaOH/HCl | q.s. to pH 6-8 |
| Purified Water | q.s. to 100 |

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

What is claimed is:

1. A method for the treatment of dry eye in a mammal, which comprises topically administering to the eye of the mammal a composition comprising a pharmaceutically acceptable carrier and 0.1-1% (w/v) of an inhibitor of the EgLN-3 enzyme, wherein the EgLN-3 inhibitor is selected from the group consisting of:

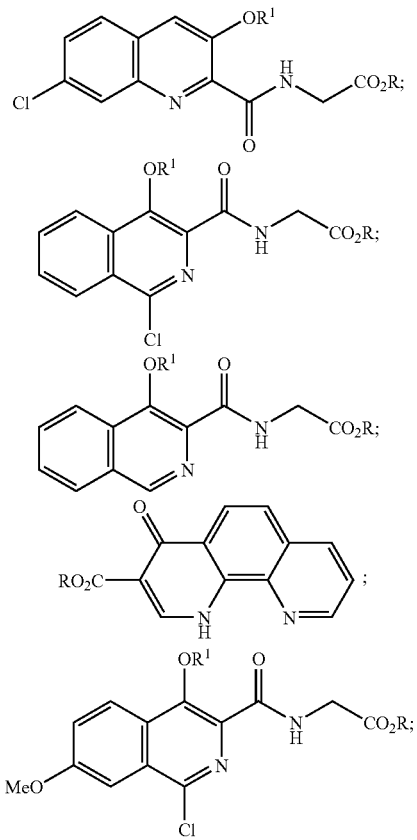

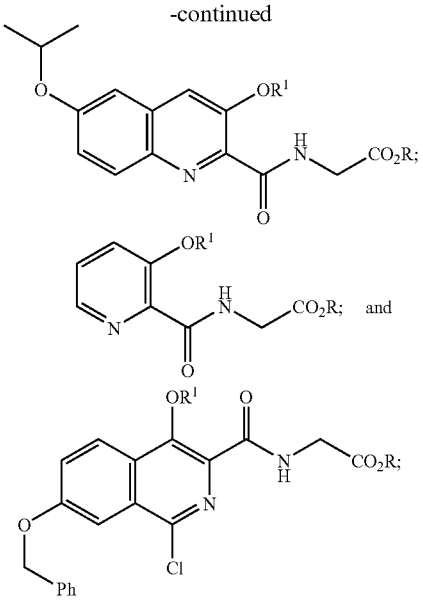

wherein:
R is H, $C_{1-6}$ straight chain or branched alkyl, phenyl, or benzyl, or $CO_2R$ forms a salt of formula $CO_2^-M^+$, with $M^+$ being $Li^+$, $Na^+$, $K^+$, or $NH_4^+$; and
$R^1$ is H, $C(O)CH_3$, or $C(O)C_6H_5$.

2. The method of claim 1, wherein the compound is selected from the group consisting of:

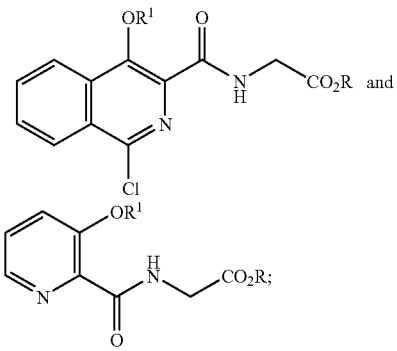

wherein:
R is H, $CH_3$, $C_2H_5$, or $i$-$C_3H_7$; and
$R^1$ is H or $C(O)CH_3$.

3. The method of claim 1, wherein
R is H, $CH_3$, $C_2H_5$, or $i$-$C_3H_7$; and
$R^1$ is H or $C(O)CH_3$.

4. The method of claim 1, wherein the pharmaceutically acceptable carrier comprises one or more ingredients selected from the group consisting of surfactants; tonicity agents; buffers; preservatives; co-solvents; and viscosity building agents.

* * * * *